United States Patent [19]

Alexander et al.

[11] Patent Number: 5,231,085
[45] Date of Patent: Jul. 27, 1993

[54] COMPOSITIONS AND METHODS FOR THE ENHANCEMENT OF HOST DEFENSE MECHANISMS

[75] Inventors: J. Wesley Alexander, Cincinnati, Ohio; Vigen K. Babayan, Waban; George L. Blackburn, Jamiaca Plains, both of Mass.; Frank B. Cerra, S. E. Edina, Minn.; John Daly, Haveford, Pa.; Mitchell T. Gersovitz, Eden Prairie, Minn.; John E. Kinsella, Ithaca, N.Y.; Jerome J. LiCari, Plymouth, Minn.; Frederick Rudolph; Charles T. Van Buren, both of Houston, Tex.

[73] Assignee: Sandoz Ltd., Basel, Switzerland

[21] Appl. No.: 837,712

[22] Filed: Feb. 19, 1992

Related U.S. Application Data

[63] Continuation of Ser. No. 421,045, Oct. 13, 1989, abandoned, which is a continuation-in-part of Ser. No. 305,877, Feb. 2, 1989, abandoned, which is a continuation-in-part of Ser. No. 265,373, Oct. 31, 1988, abandoned.

[51] Int. Cl.$^5$ ............................................. A61K 31/00
[52] U.S. Cl. ........................................ 514/44; 514/47; 514/49; 514/50; 514/51; 514/547; 514/549; 514/552; 514/558; 514/560; 514/885
[58] Field of Search ................ 514/47, 49, 50, 51, 514/547, 549, 552, 560, 558

[56] References Cited

U.S. PATENT DOCUMENTS

| | | | |
|---|---|---|---|
| 4,752,618 | 6/1988 | Mascioli et al. | 514/549 |
| 4,758,553 | 7/1988 | Ogoshi | 514/47 |

Primary Examiner—John W. Rollins
Assistant Examiner—James Oliver Wilson
Attorney, Agent, or Firm—Robert S. Honor; Melvyn M. Kassenoff; Carl W. Battle

[57] ABSTRACT

The invention provides immunostimulatory compositions comprising an aggregate immunostimulatory amount of
a) a compound associated with the synthesis of polyamines,
b) a nucleobase source,
c) omega-3 polyunsaturated fatty acids, and
d) omega-6 polyunsaturated fatty acids
the use of such compositions and their manufacture.

16 Claims, 3 Drawing Sheets

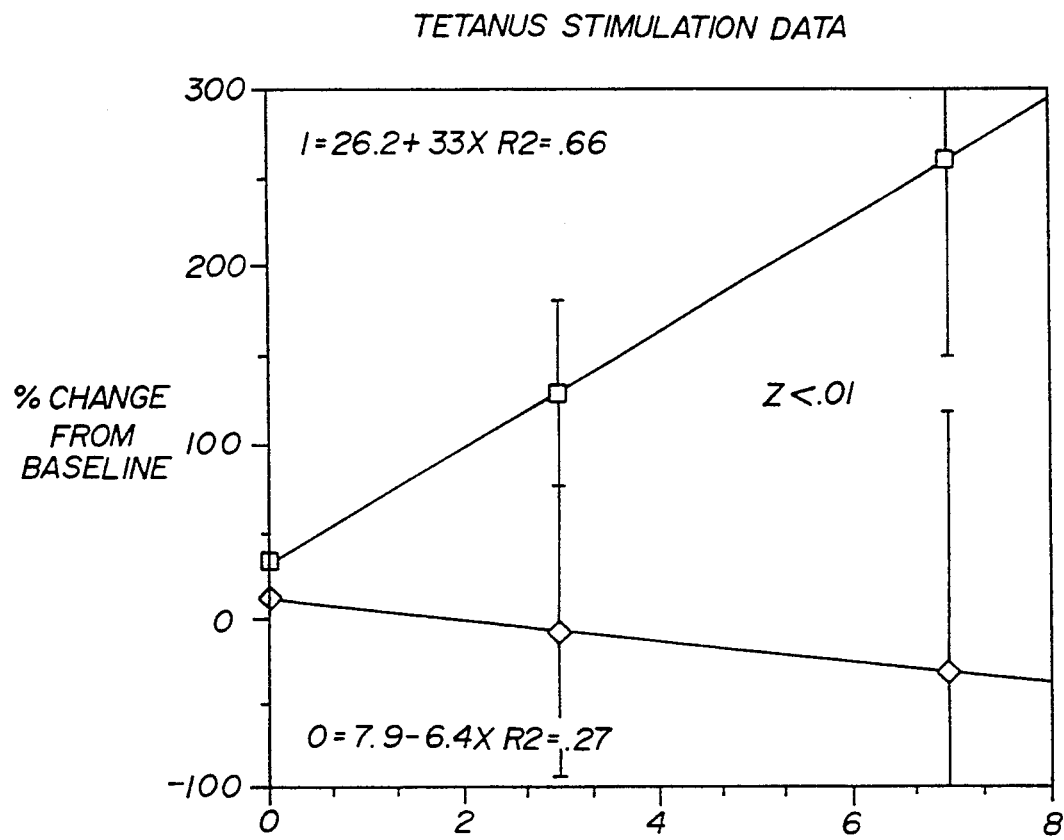

COMPOSITIONS AND METHODS FOR THE ENHANCEMENT OF HOST DEFENSE MECHANISMS

This is a continuation of application Ser. No. 07/421,045, filed Oct. 13, 1989, which in turn is a continuation-in-part of application Ser. No. 07/305,877, filed Feb. 2, 1989, which in turn in a continuation-in-part of application Ser. No. 07/265,373, filed Oct. 31, 1988, all three of which are now abandoned.

FIELD OF THE INVENTION

This invention relates to the enhancement of host defense mechanisms in mammals, e.g., immunostimulation.

BACKGROUND OF THE INVENTION

The prior art has shown that nutritional adjunctive therapy given to patients either by mouth (enteral) or by vein (parenteral) is efficacious in reversing catabolism and stimulating anabolism. This improvement in the metabolic state of the patient is believed critical to the healing process and required for patient survival. However, it has been observed the patients receiving chemically defined parenteral and enteral nutritional regimens often have compromised host defense mechanisms. This compromise of the immune system, even while the metabolic system is improving, may lead to increased morbidity and mortality as a result of sepsis and multiple organ failure.

In recent years attention has been focused on identifying the biochemicals or nutrients that are missing from all commercially available parenteral nutritional products and all commercially available defined formula enteral diets. It has been demonstrated by Rudolph and Van Buren that the addition of nucleic acids (RNA) to defined formula diets fed to animals resulted in improved host defense mechanisms. Further, Barul and Daly have shown that when arginine is fed at levels exceeding the body's need for protein synthesis, host defense mechanisms are enhanced. This is evidenced by increased blastogenesis of lymphocytes in response to mitogens in animals and man; reduced tumor appearance and incidence; increased survival in animals; and increased receptivity of cells to lymphokines.

It has also been observed that omega-6 fatty acids (polyunsaturated vegetable oils typically found as the source of lipids in nutritional products) enter the body's metabolic pathways where they serve as precursors to the family of prostaglandins associated with inflammation and suppression of host defense mechanisms. Omega-3 fatty acids (typically found in fish oils) administered to man or animals either parenterally or enterally, enter the biosynthetic pathways and are preferentially converted to the family of prostaglandins that have not been found to be either inflammatory in nature nor immunosuppressive.

Alexander has disclosed that when omega-3 fatty acids and supplemental arginine are fed to burned guinea pigs and humans, improved host defense mechanisms resulted, as determined by a reduction in the incidence of sepsis and overall morbidity.

Each of the biochemicals and nutrients cited above when administered alone provided some level of increased immunoenhancement or decreased immunosuppression in animals and humans given defined formula parenteral or enteral nutrition. However, the prior art is silent as to the administration to animals or man of combinations of these compounds either with or without increased levels of micro-nutrients for immunoenhancement.

BRIEF DESCRIPTION OF THE DRAWINGS

FIG. 3 shows the results of in vitro stimulation of peripheral blood lymphocytes with Tetanus antigen.

STATEMENT OF INVENTION

Figure 1:
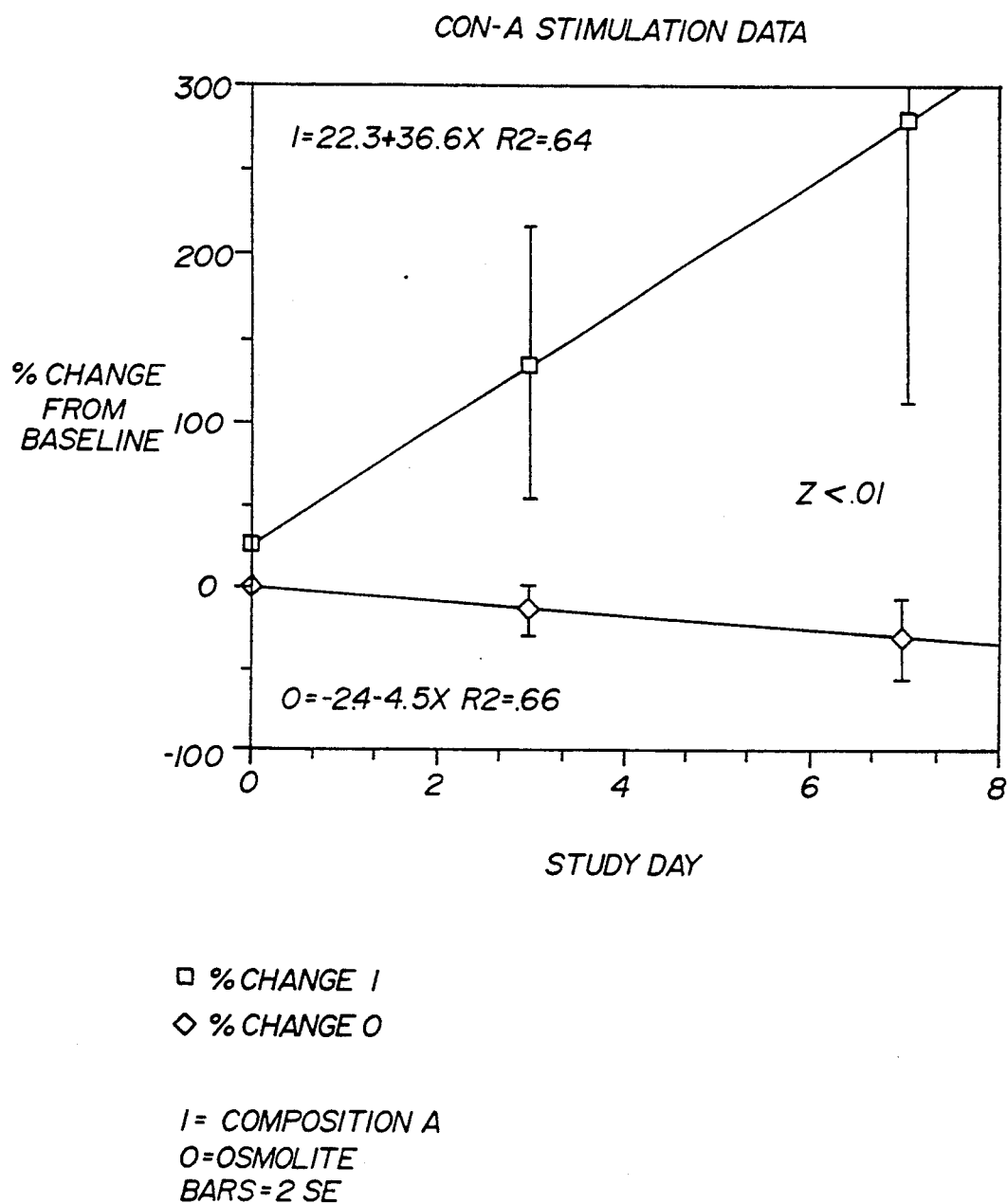
FIG. 1 shows the results of in vitro stimulation of peripheral blood lymphocytes with Con A.

This invention relates to immunostimulatory compositions and methods that enhance host defense mechanisms, e.g., to compositions enhancing the recovery of a deficient or suppressed immune function in humans.

Typically, the invention provides immunostimulatory compositions comprising an aggregate immunostimulatory effective amount of a) a compound associated with the synthesis of polyamines,
b) a nucleobase source,
c) omega-3 polyunsaturated fatty acids, and
d) omega-6 polyunsaturated fatty acids.

The term "a compound associated with the synthesis of polyamines" as used herein is intended to include, but not limited to arginine, arginine precursors, ornithine and the like, in free amino acid form or salt form; it relates in particular to arginine. Though part of the ornithine and arginine may be administered in protein form, the arginine and ornithine content of proteins will in general be so low that the contribution of any added protein source to the arginine and ornithine content of the composition of the invention can be ignored.

The amount of arginine component to be supplied may vary within wide ranges, depending on i.a. the desired treatment, subject to be treated and his needs. Thus, where the subject to be treated is an adult person (typically of ca. 60 to 75 kg body weight) a satisfactory immunostimulatory response is, in general, obtained with compositions formulated to allow a daily administration of 3 to 40 grams, preferably 10 to 30 grams, most preferred 15 to 22 grams of arginine (in free amino acid form). Ornithine and/or other compounds associated with the synthesis of polyamines, may be substituted on a 1:1 molar ratio for arginine, or used in combination with arginine.

Nucleobase sources suitable for use in the composition of the invention comprise or consist of natural nucleobases, nucleosides, nucleotides, RNA, DNA, equivalents thereof and/or mixtures comprising one or more of these compounds.

Natural nucleobases include the purines adenine and guanine as well as the pyrimidines cytosine, thymine and uracil. Where the nucleobase source is in the form of free nucleobases, it is preferably uracil.

Natural nucleosides include the ribose nucleosides adenosine, guanosine, uridine and cytidine and the deoxyribose nucleosides deoxyadenosine, deoxyguanosine, deoxythymidine and deoxycytidine.

Natural nucleotides include phosphate esters of natural nucleosides, such as the monophosphates adenylate (AMP), guanylate (GMP), uridylate (UMP), cytidylate (CMP), deoxythymidylate (dTMP) deoxycytidylate (dCMP), and diphosphates and triphosphates of natural nucleosides such as ADP and ATP.

A purified nucleobase source, such as yeast, is preferred. However, other sources such as meat and the like may be used.

The amount of nucleobase source to be administered will i.a. depend on the type of treatment desired, the subject to be treated and the like. Thus, where the subject to be treated is an adult person, a satisfactory immunostimulatory response is, in general, obtained with compositions of the invention formulated to allow a daily administration of from 0.1 to 4.0 grams, preferably 1 to 3 grams, most preferred from 1.25 to 2.5 grams of RNA, or an equivalent amount of another nucleobase source. For the purpose of this invention one weight unit of nucleobase is regarded to be equivalent with 2.5 to 3.0 weight units of RNA, DNA, nucleosides or nucleotides.

For the purpose of the invention the omega-3 polyunsaturated fatty acids (PUFA) may be in free acid form or in a form suitable for the physiological supply of omega-3 PUFAs, e.g. in triglyceride form. Examples of omega-3 PUFAs particularly appropriate for use in the compositions of the invention include eicosapentaenoic acid (EPA) and docosahexaenoic acid (DHA). Suitable sources for such omega-3 PUFAs are known. They include linseed oil and fish oils such as menhaden oil, salmon oil, mackeral oil, tuna oil and anchovy oil, in particular menhaden oil.

The amount of omega-3 PUFAs to be administered will i.a. depend on the type of treatment, the subject to be treated and the like. Thus, where the subject to be treated is an adult person a satisfactory immunostimulatory response is, in general, obtained with compositions of the invention formulated to allow a daily supply of from about 0.1 to 20 grams, preferably from 0.1 to 15 grams, most preferred from 0.15 to 10.0 grams of omega-3 fatty acids.

For the purpose of the invention the omega-6 PUFAs may be in free acid form or in a form suitable for the physiological supply of omega-6 PUFAs, e.g. in triglyceride form. Examples of omega-6 PUFAs particularly appropriate for use according to the invention include linoleic acid and arachidonic acid (ETA), linoleic acid being most preferred. Examples of suitable omega-6 PUFA sources are known in the art. They include vegetable oils. Preferred are omega-6 PUFA sources having a high linoleic acid content such as safflower oil, sunflower oil, soya oil, cotton oil and corn oil.

The amount of omega-6 PUFAs to be supplied will i.a. depend on the type of treatment, the subject to be treated and the like.

Typically, the compositions of the invention will provide for a daily supply of from 0.1 to 20 grams, preferably 0.15 to 15 grams, most preferred 0.5 to 10 grams of omega-6 PUFAs.

The compositions of the invention may be formulated in a form suitable for parenteral or enteral administration. They are particularly appropriate for enteral use, e.g. for oral administration, nasal administration and/or tube feeding. Such compositions are conveniently administered in the form of an aqueous liquid. The compositions of the invention suitable for enteral application are accordingly preferably in aqueous form or in powder form, whereby the powder is conveniently added to water prior to use. For use as tube feeding, the amount of water to be added will i.a. depend on the patient's fluid requirements and condition.

The composition of the invention may comprise vitamins, mineral, trace elements as well as additional nitrogen, carbohydrate and fatty acid sources.

According to a preferred embodiment of the invention, the compositions of the invention are in the form of a liquid complete formula diet, such that, when used as sole nutrition source essentially all daily caloric, nitrogen, fatty acid, vitamin, mineral and trace element requirements are met.

In general, the daily caloric amount to be supplied to adult person will lie in the range of 750 to 3500 kcal/day, in particular of 1000 to 2000 kcal/day. Depending on the patient's condition, e.g. for use against post-surgical trauma, it may be desirable to initially (for example from day 1 to 5) administer a hypocaloric daily amount and to increase the energy supply thereafter to meet the normal daily caloric requirements. The contribution of the nitrogen source, carbohydrate source and lipid source to the total daily caloric may vary within wide ranges. In preferred compositions of the invention the carbohydrate source provides for 40 to 70% of the total energy supply and, the nitrogen and fatty acid source each for 15 to 30% of the total energy supply of the composition.

Examples of suitable nitrogen sources include nutritionally acceptable proteins such as caseinates, or protein hydrolysates.

Examples of suitable carbohydrate sources include maltodextrins.

Examples of suitable fatty acid energy supply sources include triglyceride sources.

Preferred examples of triglyceride sources suitable for use in the composition of the invention include triglyceride oils supplying the desired amounts of omega-3 and omega-6 fatty acids and which are rich in the medium chain fatty acid residues (i.e. residues of $C_6$ to $C_{12}$ fatty acid) and/or mono-unsaturated fatty acid residues. Preferably the triglyceride source provides a balance between the various types of unsaturated fatty acids, in particular between polyunsaturated omega-3, polyunsaturated omega-6 and mono-unsaturated omega-9 fatty acids, to manipulate the eicosanoids produced.

Suitable sources of such triglycerides are e.g. physical mixtures of LCT (long chain triglycerides) and MCT (medium chain triglycerides) or structured lipids (triglycerides).

The MCT and LCT suitable for use in the physical mixtures may be used in pure form or in the form of oils rich in MCT or LCT. The LCT sources, as stated earlier, are conveniently rich in essential fatty acid residues. Suitable MCT sources are e.g. vegetable oils, including kernel oils such as palm kernel oil, coconut oil, balassu oil, cohune oil, tucum oil and fractions thereof. The preferred MCT vegetable oil is coconut oil.

Preferred compositions of the invention comprise triglycerides providing for a daily supply of from 1 to 30 grams, preferably of 2 to 20 grams, most preferred of 8 to 15 grams of medium chain fatty acids, in particular of lauric acid.

Particularly preferred compositions of the invention comprise triglycerides providing daily supply of from 1 to 30 grams, preferably of 5 to 25 grams, most preferred of 5 to 20 grams of mono-unsaturated fatty acids. Suitable sources for mono-unsaturated fatty acids provide omega-9 mono-unsaturated fatty acids and are rich in oleic acid. Examples of such sources comprise olives, canola, safflower (hybrids) and sunflower (hybrids).

Examples of vitamins suitable for incorporation in the composition of the invention include vitamin A, vitamin D, vitamin E, vitamin K, vitamin C, folic acid, thiamin, riboflavin, vitamin $B_6$, vitamin $B_{12}$, niacin, biotin and panthotenic acid in pharmaceutically acceptable form.

Examples of mineral elements and trace elements suitable for incorporation in the composition of the invention include sodium, potassium, calcium, phosphorus, magnesium, manganese, copper, zinc, iron, selenium, chromium and molybdenum in pharmaceutically acceptable form.

In particular, the compositions of the invention will preferably comprise beta-carotene (vitamin A), vitamin E, vitamin C, thiamine, vitamin $B_{12}$, choline, selenium and zinc in pharmaceutically acceptable form.

Typically, the amount of composition of the invention suitable to meet the daily requirements of a patient suffering from depressed host defense mechanisms will comprise from 3 to 40 grams of arginine, or a physiologically equivalent amount of another compound associated with the synthesis of polyamines or of a mixture of such compounds in association with from 0.1 to 4.0 g of nucleobase source, of 0.1 to 20 g of omega-3 fatty acids, and from 0.1 to 20 g omega-6 fatty acids. Such unit daily amount will conveniently provide an energy supply of from 750 to 3500 kcal/day.

The immunostimulatory compositions of this invention are suitable for use in patients who suffer from depressed host defense mechanisms, e.g. in patients who suffer from depressed host defense mechanisms as a result of post-surgical trauma, cancer, chemotherapy/radiation therapy, sepsis, trauma, burns, immunosuppressive drug therapy, malnutrition, transfusion induced immunosuppression and the like.

It has indeed been observed that the body, when under severe stress, cannot readily mobilise the nutrients necessary to secure a normal immune function. The administration of the composition of the invention allows to maintain, restore and enhance the immune function where desired. The immune system reacts surprisingly quick and favourable to the administration of the composition of the invention.

Such compositions may accordingly be employed to enhance a depressed host defense mechanism, to restore a normal immune function in a human with a deficient immune response, to enhance the development of the immune system in a developing human, to enhance a senescent immune system of a human and the like.

The invention accordingly also provides the composition of the invention for use in a method of maintaining or stimulating the immune system of a patient, in need of such treatment.

The invention further provides the use of
a) a compound associated with the synthesis of polyamines,
b) a nucleobase source,
c) omega-3 polyunsaturated fatty acids, and
d) omega-6 polyunsaturated fatty acids,
in a method of manufacturing a dietary composition for the stimulation of the immune function in the human body.

The composition of the invention may be obtained in a manner known per se, e.g. by admixing the ingredients.

The following examples illustrate the invention:

EXAMPLE 1

| COMPOSITION A (1 kcal/cc) | |
|---|---|
| | per 1500 cc |
| Nitrogen Source | |
| Intact Protein (Na/Ca Caseinates) | 65.0 g |
| Arginine | 18.75 g |
| Carbohydrate Source | 197.6 g |
| Maltodextrins | |
| Lipid Source | |
| Structured Lipids (Captex ® 710A) | 25.0 g |
| Menhaden Oil | 16.75 g |
| (refined, unhydrogenated) | |
| Typical Fatty Acid Profile | |
| (MCT 8–13 g, e.g. 11.5 g) | |
| (Linoleic acid 2.5–4.5 g) | |
| (eicosapentaenoic acid -(EPA)- 1.0–2.0 g) | |
| (docosahexaenoic acid -(DHA)- 0.25–1.00 g) | |
| (Monounsaturated fatty acids 8–11 g, e.g. 10 g) | |
| (Polyunsaturated fatty acids 6–10 g, including e.g. 3.6 g omega-6 PUFA and 3.0 g omega-3 PUFA) | |
| RNA Source | 1.88 g |
| Yeast RNA | |
| Typical Nucleotide Profile | |
| (Uracil 0.34–0.47 g) | |
| (Cytosine 0.15–0.28 g) | |
| (Guanine 0.56–0.77 g) | |
| (Adenine 0.53–0.649 g) | |
| (Thymine 0.01–0.09) | |

| Vitamin and Minerals | | % USRDA[1] | % NASRDA[2] |
|---|---|---|---|
| Vitamin A (IU) | 10,000 | 200 | 200 |
| Vitamin D (IU) | 400 | 100 | 100 |
| Vitamin E (IU) | 90 | 200 | 300 |
| Vitamin K (mcg) | 100 | *** | 70–140+ |
| Vitamin C (mg) | 120 | 200 | 200 |
| Folic Acid (mcg) | 600 | 150 | 150 |
| Thiamin (mg) | 3.0 | 200 | 200 |
| Riboflavin (mg) q | 2.55 | 150 | 150 |
| Vitamin B6 (mg) | 2.2 | 100 | 110 |
| Vitamin B12 (mcg) | 12.0 | 200 | 200 |
| Niacin (mg) | 30.0 | 150 | 150 |
| Choline (mg) | 400 | *** | 400–900++ |
| Biotin (mg) | 0.3 | 100 | 0.1–0.2+ |
| Pantothenic (mg) | 10.0 | 100 | 4–7+ |
| Sodium (g) (1.1 to 2.5) | 1.6 | *** | 1.1–3.3+ |
| Potassium (g) (1.9 to 3.0) | 1.9 | *** | 1.87–5.629+ |
| Chloride (g) (1.7 to 3.0) | 2.0 | *** | 1.7–5.1+ |
| Calcium (g) | 1.2 | 120 | 120 |
| Phosphorous (g) | 1.2 | 120 | 120 |
| Magnesium (mg) | 400 | 100 | 100 |
| Iodine (mcg) | 150 | 100 | 100 |
| Manganese (mg) | 3.0 | *** | 2.5–5.0+ |
| Copper (mg) | 2.5 | 125 | 2.0–3.0+ |
| Zinc (mg) | 22.5 | 150 | 150 |
| Iron (mg) | 18.0 | 100 | 100 |
| Selenium (mcg) | 150 | *** | 50–200+ |
| Chromium (mcg) | 150 | *** | 50–200+ |
| Molybedenum (mcg) | 300 | *** | 150–500+ |

Water 75–80% by weight of the total composition

Nitrogen Source 335 kcal - 22% of the total caloric amount
Carbohydrate Source 790 kcal - 53% of the total caloric amount
Lipid Source 375 kcal - 25% of the total caloric amount
[1]USRDA United States Recommended Dietary Allowances
[2]NAS RDA National Academy of Sciences Recomended Dietary Allowances
+Estimated Safe and Adequate Daily Dietary Indexes of Selected Vitamins and Minerals, NAS 1980 9th RDA
++Estimated range of intake
***No USRDA established

EXAMPLE 2

This study was undertaken in Intensive Care Unit (IUC) patients with prolonged ICU stays after trauma, sepsis or major general surgery.

Material and Methods

This clinical protocol was of randomized, double-blind, prospective design. It was approved by the Human Investigations Committee of the University of Minnesota. All patients were entered after obtaining written, informed consent.

The inclusion criteria were: ICU patients, male or female, who were 21-80 years old and had sustained a surgical event for which they were admitted into, and continued in, the ICU. These events included trauma, major elective general surgery, and surgical infections. Each patient had to be minimally to moderately malnourished; under moderate metabolic stress; be judged suitable for enteral nutrition for 7-10 days; and be judged to be able to tolerate all of the nutrition support by the enteral route.

All patients received H2-receptor antagonists as part of a regimen of stress ulcer prophylaxis. All other care was delivered in accordance with clinical need.

There was no specific precipitating event for inclusion into the protocol. Rather, each patient had to meet the above criteria. Therefore, they could be in the ICU a variable period of time prior to entering the study. This parameter is called: Days to Entrance. During this time, each was maintained on parenteral nutrition begun within 24 hours of injury and having the general formula: 1.5-2.0 g/kg/day of amino acids, 1.0 g/kg/day of fat, and the remaining calories as glucose at 30-35 total Kcals/kg/day. enteral nutrition was considered, a feeding tube was placed, and the parenteral nutrition stopped. The indications for tube feeding were: an adequately functioning gut, and suitable access to that functioning gut. The feeding tube was a nasoenteric, weighted feeding tube placed past the gastric pylorus and into the duodenum under fluoroscopy. The patient was then randomized by the research pharmacy by opening a sealed envelop, reading the instructions, and assigning the patient to the appropriate group. The blinded feedings were delivered from the research pharmacy to the ICU and given by continuous infusion with a pump. Tube feeds were started at full strength at 25 ml/hr and progressed at 25 ml/hr increments every 12 hours until the required volume per day was achieved. This time from inception of tube feeds to achieving the full dose is called; Days to Goal. Study Day 1 was the first day the patient was fully receiving the estimated caloric requirement. The patient continued in the study until 7-10 days of full therapy was delivered.

Two nutritionally complete diets were used in the study. Composition A, according to the invention, and, as a Standard, Osmolite® HN, lactose-free, caseinate based enteral feeding formula commercially available from Ross Laboratories.

The amount of formula given was calculated from the energy expenditure. Energy expenditure was calculated as the basal energy expenditure (BEE) using the Harris-Benedict equations; and using 150% of BEE as the amount of calories necessary on a daily basis.

On study days 0,3 and 7-10, the following parameters were obtained; serum glucose, blood urea nitrogen (BUN), creatinine, liver function tests, platelet count, prothrombin time, triglyceride, albumin and a plasma transferrin. Additional blood was drawn for in-vitro immune stimulation studies; Con-A, HA, and Tetanus. Urine and stool were collected on a daily basis for total nitrogen analysis. The chemistry determinations were done by standard laboratory methods. The immune function studies were done in the Immunobiology Research Laboratories of the University of Minnesota. Nitrogen balance was calculated as nitrogen in −nitrogen out; where nitrogen out=urine nitrogen+stool nitrogen+1.0. Values were corrected for BUN and weight change.

All completed patients were subjected to data analysis. A treatment failure wasconsidered a patient who experiences severe intolerance to the diet that precludes administration of the enteral nutrition, or has an adverse reaction to the diet.

Treatment failures and dropouts were excluded from the data analysis.

The data on entrance characteristics was analysed by 1-way analysis of variance. The data over the study interval, except the immune function studies was analysed by a 2-way analysis of variance for diet type and time (study day). The immune function tests were analysed by regression analysis. Each data point for each test was calculated as the per cent change from baseline on Day 0 of the study. A regression line was then calculated for each patient in each test in both control (Osmolite® HN) and experimental Composition A (as defined in Example 1) groups. These regressions were then treated as a population for each variable and a Z-score determined for both control and experimental groups in each immune function test to ascertain if the change over time was significantly different from 0. A Z-score was then calculated between the control and experimental groups for each test to ascertain if the two lines were significantly different from each other. In all cases, significance was defined as $P<0.05$.

Results

There were 11/13 completed patients in the Composition A group; and 9/9 in the Osmolite® HN group. The two noncompleters were both dropouts; one self-withdrew on Day 1, and one had feeds discontinued for more than 24 hours. There were no statistical differences between the groups. The clinical conditions were also the same.

all patients had sepsis or sepsis syndrome (see Bone R. C. et al in Crit. Care Med. 17 389-393 (1989 and Cerra FB in Surery 101, 1-14 (1987), following trauma, sepsis, or major general surgical procedure.

The outcome data are consistent with the view-point that diet composition is important not only in influencing classic nutritional outcomes such as nitrogen balance, but in influencing other systemic, and perhaps nutrient specific effects such as the in vitro lymph lymphoproliferative response to Con A, HA and Tetanus antigen.

There were no demonstrable differences in feeding administered or in the nutritional results of the feedings. Likewise, there were no differences in the mortality and length of stay observations.

Figure 2:
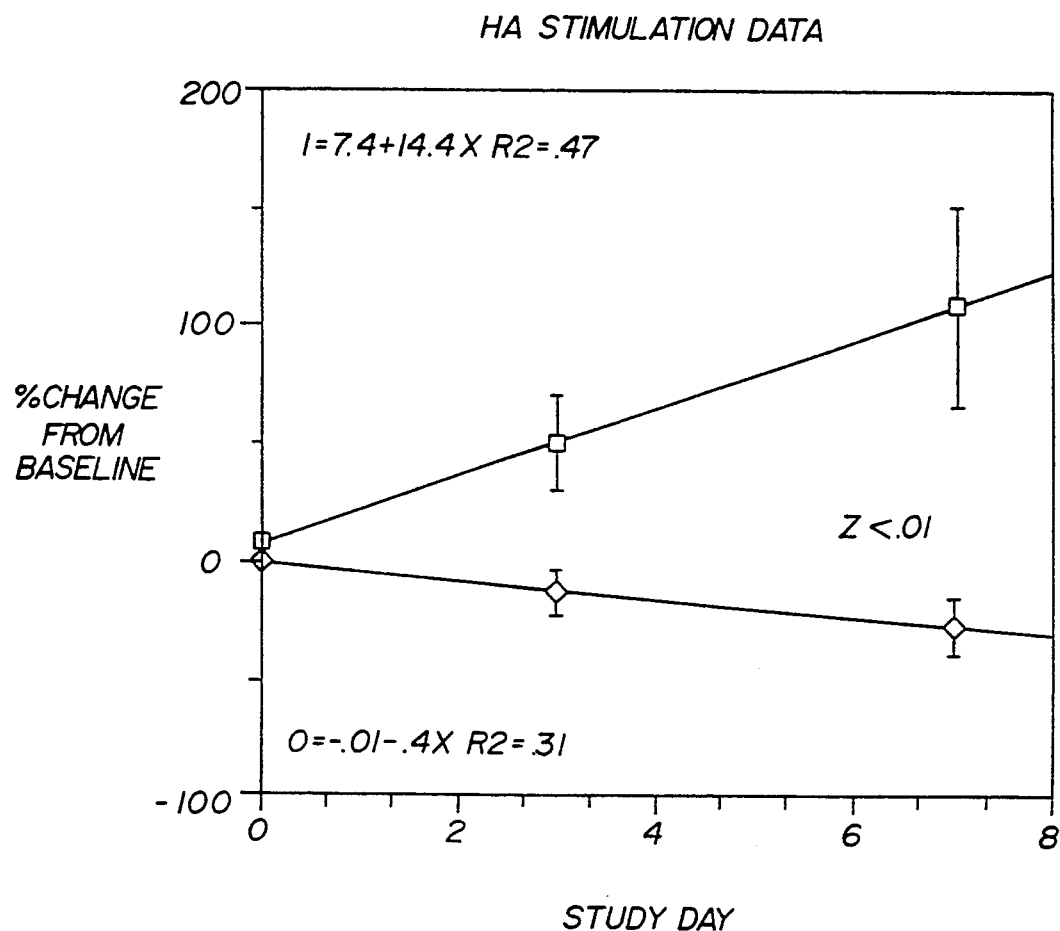
FIG. 2 shows the results of in vitro stimulation of peripheral blood lymphocytes with HA.

The results of in vitro stimulation of periphereal blood lymphocytes with Con A, HA and Tetanus antigen are presented in FIGS. 1, 2 and 3 resp. In all three cases, the control diet was associated with a downward trend, while that with the diet of the invention (Composition A) was associated with increased responsiveness.

EXAMPLE 3

This example shows the results of a prospective randomized trail comparing the effects of a dietary enteral formulation according to the invention, versus a standard enteral diet (Osmolite® HN) in patients undergoing major operation for upper gastrointestinal malignancies.

Materials and Methods

Adult patients with gastrointestinal (GI) malignancies undergoing major abdominal operation were stratified based on the extent of their weight loss (less than 10% of usual body weight vs. greater than or equal to 10% of usual body weight) and the blood transfusions they had received during their operation (none vs. greater than or equal to 1). Patients were then randomized to one of two treatment groups. Group I patients received enteral alimentation with Composition A (defined hereinbefore) whereas Group II patients received Osmolite® HN®.

At the time of the opertion, all patients underwent procedures as indicated by their primary site and stage of disease. A needle-catheter jejunostomy was placed in the proximal jejunum. Blood and fluid replacement was continued intravenously as clinically indicated for each patient. At 11.00 AM on the first postoperative day, jejunostomy patients were randomly assigned to receive either Composition A or Osmolite HN®. The formulas were coded and the investigators were blinded until after data analysis was complete.

Gastrointestinal symptomatology was assessed and recorded daily.

All patients were managed with some tube nasogastric drainage, with the tube being removed when clinically indicated. Other than clear liquids taken orally, patients received no nutrition during the first seven postoperative days. All patients received intravenous (IV) fluids, 5% dextrose and 0.5% normal saline solution and other electrolytes as clinically indicated.

Body weight of all patients was assessed daily. All intravenous and enteral intake was measured and a caloric/nitrogen ratio was calculated. The urine was collected for each 24-hour period; urine nitrogen content was measured by the Kjeldahl technique and creatinine was measured by an automated system (Technicon, Tarrytown, N.Y.). Urine nitrogen levels were calculated for each 24-hour period by measuring urine creatinine excretion and correcting for change in serum urea nitrogen levels. No attempt was made to collect the fecal output. In the absence of diarrhea, a significant amount of stool was not excreted until oral intake was resumed after day 7.

Immune Function Studies

Blood was collected at 8 AM on the day before operation and on the first and seventh postoperative days. Peripheral blood mononuclear cells (PBMC) were isolated from heparinized venous blood by Ficoll-Hypaque density gradient centrifigation. Cells were washed three times with Hanks Balanced Salt Solution (HBSS), resuspended in complete medium, and counted. Cell viability was determined by trypan blue dye exclusion. Freshly isolated PBMC were suspended in a concentration of $1 \times 10^6$ ml in Roswell Park Memorial Institute (RPMI) 1640 medium supplemented with 10% heat inactivated pooled normal blood type A serum, two mM glutamine, 100 units per ml penicillin and 100 mg/ml streptomycin. PBMC were cultured at a concentration of $1 \times 10^6$ ml in flat-bottomed microtiter plates with/without 10 mg/ml con A or phytohemogglutinin (Sigma, St. Louis, Mo.). The cultures were incubated in a humidified incubator at 37° C. in 5% $CO_2$ for three days. Fourteen hours before harvesting, one microcurie of tritiated thymidine was added to each well and the radioactivity in the pellets counted in liquid scintillation counter (Tricar, Model 500, Packard, Sterling, Va.). Data is expressed as a stimulation index. The stimulation index is equal to mean counts per minute of stimulated lymphocytes over the mean counts per minute of unstimulated lymphocytes. Data are reported as the mean ± the standard error of the mean. Statistical significance was determined at the $p < 0.05$ level by Students unpaired t-test.

RESULTS

Patient Characteristics and Metabolic Data

Upon entry into the study, patient characteristics were homogeneous. 31 Patients were studied. The mean age for patients in the Composition a (I) and Osmolite® HN (II) groups were 63 and 66 years respectively. The preoperative diagnosis and operative procedures were similar between the two groups. Postoperative total caloric intake was similar between treatment groups.

Immune Data

The mean stimulation indices to Conconavalin A (Con A) and lymphocyte response to the nitrogen phytohemaglutinin (PHA) are shown in the following tables:

| | IMMUNE FUNCTION: PHA Mean Stimulation Index ± SD | |
|---|---|---|
| Group | I | II |
| Preoperatively | 175 ± 119 | 135 ± 103 |
| Postoperative day 1 | 90 ± 86 | 84 ± 79 |
| Postoperative day 7 | 188 ± 109 | 83 ± 61* |

*P = 0.01

| | IMMUNE FUNCTION: Con A Mean Stimulation Index + SD | |
|---|---|---|
| Group | I | II |
| Preoperatively | 29 ± 31 | 27 ± 23 |
| Postoperative day 1 | 15 ± 22 | 13 ± 12 |
| Postoperative day 7 | 24 ± 33 | 10 ± 8* |

*P = 0.06

EXAMPLE 4

Effect of Dietary Components on the in Vivo Cell Mediated Immune Response in Mice

Materials and Methods

Animals:

Approximately 12 week old, weight matched Balb/c female mice (H-$2^b$) (NIH-Jax Labs) were used as recipients and syngeneic spleen cell donors and C57b1/6 female mice (H-$2^d$) as allogeneic spleen cell donors. After receiving the animals they were acclimatized in our animal housing facility for several weeks before starting them on various experimental diets. They were maintained on a 12 hour light and dark cycle with food and water ad libitum. Animals were housed 5 per cage and experimental animals observed daily and body weights recorded weekly.

Diets

The following were used:

F; Standard laboratory chow supplied by Purina under code number 5008 and comprising 23.5% by weight of a protein source from soybean, fish bone meal and milk, DF: a protein free diet available from Purina under code number 5765c, wherein the energy supply is adjusted with carbohydrate, NF: Basal diet, nucleotide free diet supplied by Purina under code number 5775 and comprising 21% by weight of casein as its protein source. NF is isocaloric and isonitrogenous with composition F.

NFR: NF supplemented with 0.25% yeast RNA.

M1: A mixture of 86.2% by weight of an experimental non-fat 90% formula powder consisting of 21 parts casein, 15 parts sucrose, 3 parts Solka Floc (a fibre), 2 parts Vitamin mix, 5 parts mineral mix, 0.15 parts dL-Methionine, 0.20 parts choline chloride and 43.65 dextrin (hereinafter purina 5758 M-T) with 0.57% of RNA, 5.75% of arginine and 7.5% of menhaden oil.

M2: A combination comprising 86.93% by weight of Purina 5785 M-T, 0.57% of RNA, 5.62% of arginine, 4.99% of menhaden oil and 1.89% of safflower oil including the following NF and NFR based diets, supplemented with glutamine or alanine:

NF+2% glutamine
NF+4% glutamine
NFR+2% glutamine
NFR+4% glutamine
NF+4% alanine
NF+8% alanine
NFR+4% alanine Ingredients were mixed in a Kitchen Aid mixer and enough de-mineralised water added to make a thick dough which is then flattened on cookie sheets with the help of a rolling pin. Dough-flats were then cut into small patties using a pizza cutter.

All the diets were frozen in ziplock freezer bags until they were used as necessary. Fish oil containing diet bags were fluxed with nitrogen gas before storage.

Feeding schedule and PLN Assay (popliteal lymph node assay). All animals were weighed on day 0. Then one group of animals was fed chow diet (F) throughout the experimental period. All other animals were fed protein-free (PF) diet for about 7 days and when they lost about 20% of their body weights, all animals were inoculated into one hind footpad with $1 \times 10^7$ syngeneic Balb/c irradiated (3000 R) spleen cells in 50 μl. volume. The contralateral foodpad received $1 \times 10^7$ allogeneic C57B1/6 irradiated (3000 R) spleen cells in 50 μl. volume. Mice were inoculated under ether anesthesia. On the same day, PF diet fed animals were divided randomly into several groups receiving the above mentioned experimental diets. On 7th day of inoculation, animals were sacrificed and the popliteal lymph nodes removed and weighed on Mettler balance (HL-52). The results of Stimulation Index are calculated as follows:

$$\text{Stimulation Index } (S.I.) = \frac{\text{Weight of allo-stimulated } PLN}{\text{Weight of syn-stimulated } PLN}.$$

Statistics:

Statistical analysis was performed by two tailed T-test method with results of dietary groups compared to those of NF basal diet. A 95% level of significance was used throughout.

RESULTS

The results of the PLN assay are summarized in the following table:

| Diet | PLN ASSAY Allo (mg) | Syn (mg) | Delta (mg) | S.I. |
|---|---|---|---|---|
| F | 5.29 ± .44 | 1.64 ± .09 | 3.65 ± .52* | 3.30 ± .42* |
| .PF-F | 4.09 ± .45 | 1.47 ± .40 | 2.61 ± .39 | 3.31 ± .60 |
| .PF-NF | 3.44 ± .37 | 1.66 ± .11 | 1.78 ± .32 | 2.07 ± .20 |
| .PF-NFR | 5.07 ± .79 | 1.20 ± .20 | 3.86 ± .75* | 4.53 ± .82* |
| .PF-PF | 1.37 ± .18 | 1.00 ± .05 | 0.38 ± .16* | 1.38 ± .15* |
| .PF-NF + 2% Glutamine | 3.76 ± .30 | 1.31 ± .13 | 2.44 ± .24 | 2.91 ± .20* |
| .PF-NF + 4% Glutamine | 3.48 ± .40 | 1.6 ± .12 | 1.88 ± .39 | 2.2 ± .25 |
| .PF-NFR + 2% Glutamine | 3.78 ± .31 | 1.68 ± .16 | 2.1 ± .44 | 2.37 ± .34 |
| .PF-NFR + 4% Glutamine | 4.58 ± .38 | 2.40 ± .27 | 2.17 ± .55 | 2.05 ± .39 |
| .PF-NF + 4% Alanine | 3.31 ± .32 | 1.62 ± .13 | 1.68 ± .34 | 2.09 ± .28 |
| .PF-NF + 8% Alanine | 4.56 ± .44 | 1.6 ± .17 | 2.96 ± .36* | 2.93 ± .33 |
| .PF-NFR + 4% Alanine | 3.53 ± .29 | 1.58 ± .23 | 1.95 ± .25 | 2.35 ± .25 |
| .PF-M1 | 3.72 ± .31 | 1.84 ± .24 | 1.88 ± .51 | 2.24 ± .45 |
| .PF-M2 | 6.03 ± .68 | 1.26 ± .06 | 4.77 ± .63* | 4.77 ± .40* |

*p < 0.05 As compared to PF NF group
N = 5/Group
Day 0 Started PF diet
Day 8 Changed to Special Diets and injected PLN
Day 15 PLN Harvested In this animal model, severe protein deprivation induced malnutrition was achieved by the initial PF diet feeding, as evidenced by weight loss and general morbidity with hunched back and ruffled coat appearance. The immunologic consequence of this protein deprivation is seen in the decreased in vivo PLN response of PF dietary hosts to alloantigenic challenge as compared to basal (NF) diet fed hosts (p<0.05%) and chow fed hosts. In basal NF diet fed hosts protein content of diet helps regain the body weight and general appearance to the original levels. There is some increase in the PLN response, but significantly lower than Chow or NFR dietary hosts. Conversion to protein supplemented diets helps the hosts to restore body weights to the levels of chow fed animals.

Glutamine, Alanine and combinations of RNA, Arginine and fats (fish oil and safflower oil) were tested viz. M1 and M2. Glutamine at 2% and 4% conc. (w/w) were tested and Alanine at 4% and 8% conc. (w/w) were used to make isonitrogenous controls.

The PLN responses in glutamine and alanine in the doses tested were effective in restoring the lost body weight and general health status, but they were not able to improve or restore immune function as indicated by their PLN response.

Diet M1 (which contained only fish oil as the fat source) was unable to restore PLN response but diet M2 (comprising omega-3 and omega-6 PUFAs) was significantly more effective in restoring the immune response with a PLN S.I. of 4.77±0.4 as compared with NF diet PLN S.I. of 2.07±0.20.

We claim:

1. An immunostimulatory composition comprising, for the enhancement of depressed host defense mechanism as a result of trauma, cancer, chemotherapy, radiation therapy, sepsis, surgery, burns, immunosupressive drug therapy, malnutrition and transfusion induced immunosuppression, in a daily dosage form:
   a) 3 to 40 grams of arginine, ornithine or amino acids salts or salts thereof;
   b) 0.1 to 4.0 grams of RNA or an equivalent amount of nucleobase, nucleoside, nucleotide, DNA or mixtures thereof;
   c) 0.1 to 20 grams of omega-3 polyunsaturated fatty acids. and
   d) 0.1 to 20 grams of omega-6 polyunsaturated fatty acids.

2. A composition according to claim 1, comprising,
   a) 10 to 30 grams of arginine, ornithine or amino acids or salts thereof;
   b) 1 to 3 grams of RNA or an equivalent amount of nucleobase, nucleoside, nucleotide, DNA or mixtures thereof;
   c) 0.1 to 15 grams omega-3 polyunsaturated fatty acids; and
   d) 0.15 to 15 grams of omega-6 polyunsaturated fatty acids;

3. A composition according to claim 1, comprising,
   a) 15 to 22 grams of arginine, ornithine or amino acids or salts thereof;
   b) 1.25 to 2.5 grams of RNA or an equivalent amount of nucleobase, nucleoside, nucleotides DNA or mixtures thereof;
   c) 0.15 to 10 grams of omega-3 polyunsaturated fatty acids; and
   d) 0.5 to 10 grams of omega-6 polyunsaturated fatty acids.

4. A composition according to claim 1, comprising, from 1 to 30 grams, of mono-unsaturated fatty acids.

5. A composition according to claim 1, comprising, from 1 to 30 grams, of medium chain fatty acids.

6. A composition according to claim 1 in parenteral or enteral administration form and providing in one unit dose an energy supply of from 750 to 3500 kcal/day.

7. A composition according to claim 6, providing an energy supply of from 1000 to 2000 kcal/day.

8. A composition according to claims 6 or 7 in complete formula diet form, satisfying essentially all daily caloric, nitrogen, fatty acid, vitamin, mineral and trace element requirements.

9. A composition according to claim 8, which comprises a carbohydrate source providing for 40 to 70%, a nitrogen source providing for 15 to 30% and a fatty acid source providing for 15 to 30% of the total energy supply of the composition.

10. The composition of claim 1 wherein said omega-3 polyunsaturated fatty acids are selected from the group consisting of eicosapentaenoic acid and docosahexaenoic acid.

11. The composition of claim 1 wherein said omega-3 polyunsaturated fatty acids are from sources selected from the group consisting of linseed oil and fish oil.

12. The composition of claim 11 wherein said fish oil is selected from the group consisting of menhaden oil, salmon oil, mackeral oil, tuna oil and anchovy oil.

13. The composition of claim 1 wherein said omega-6 polyunsaturated fatty acids are selected from the group consisting of linoleic acid and arachidonic acid.

14. The composition of claim 1 wherein said omega-6 polyunsaturated fatty acids are from sources selected from the group consisting of safflower oil, sunflower oil, soya oil, cotton oil and corn oil.

15. A method of stimulating the immune system of a mammal which comprises administering to such mammal an immunostimulatory amount of a composition of claim 1.

16. The method of claim 15 wherein stimulation of said immune system results in an increase in lymphocyte cells.

* * * * *